United States Patent [19]

Cecic et al.

[11] Patent Number: 4,508,714

[45] Date of Patent: Apr. 2, 1985

[54] ORGANIC SCALP LOTION

[76] Inventors: Tihomir Cecic; Norma Cecic, both of 8641 NW. 23rd St., Pembroke Pines, Fla. 33024

[21] Appl. No.: 551,306

[22] Filed: Nov. 14, 1983

[51] Int. Cl.³ ............................................. A61K 35/78
[52] U.S. Cl. ................................................. 424/195.1
[58] Field of Search ........................................ 424/195

[56] References Cited
PUBLICATIONS

Steinmetz—Code & Vegetabilis, 1957, No. 941.

*Primary Examiner*—Albert T. Meyers
*Assistant Examiner*—John W. Rollins, Jr.
*Attorney, Agent, or Firm*—Oltman and Flynn

[57] ABSTRACT

An organic scalp lotion comprising a mechanically combined mixture of Tincture of Cinchona, Tincture of Quillaia, Tincture of Eucalyptus, ethyl alcohol and distilled water. The lotion has been found to be highly effective for treatment of seborrhea, for cleansing of the hair and the scalp and for improvement in the overall appearance of the hair when applied externally.

1 Claim, No Drawings

ORGANIC SCALP LOTION

BACKGROUND OF THE INVENTION

The invention is related to skin lotions, and more particularly to lotions having a therapeutic, hygienic and cosmetic benefit when used on the scalp.

Lotions for hair care have long been known and used, especially lotions with detergent properties for cleansing and washing, lotions imbued with fragrant constituents, lotions with antiseptic or anti-fungal ingredients for suppressing unwanted micro-organisms that often find a suitable growing condition on the human hair and on the scalp.

SUMMARY OF THE INVENTION

The invention is a composition of naturally occurring organic ingredients that is beneficial for use as a hair lotion. The lotion, according to the teachings of the invention, is beneficial in that it combines the astringent effects of one ingredient with the detergent, cleansing effect of another ingredient and the anti-biotic effects of still another ingredient.

DETAILED DESCRIPTION OF THE INVENTION

The invention is a composition of naturally occurring substances, that in combination have been found to be beneficial to the maintenance of hair hygiene to a degree that compares very favorably with that of other hair and scalp lotions as determined empirically by its use.

The substances used in the composition, according to the teachings of the invention are (a) Tincture of Cinchone, (b) Tincture of Quillaia, (c) Tincture of Eucalyptus, (d) Alcohol and (e) distilled water.

Tincture of Cinchona is prepared by percolating the powdered bark of Cinchona plants (C. Calisaya, C. Officinalis, C. Micrantha, C. Pubescens, C. Pitayensis), trees of the Rubiacea family, indigenous of the South American Andes. This extract is standardised to contain 10% total alkaloids. Tincture of Cinchona contains 1% of total alkaloids and is made by suitably diluting the extract with 70% alcohol.

By far the most important active constituent of Cinchona is the alkaloid Quinine. In addition, 29 other alkaloids have been isolated, of which Cinchonidine, which like Quinine is levo-rotatory, and the two dextro-rotatory, (i.g. levo-rotary is left-turning and dextro-rotary is right-turning in polarized light analysis) alkaloids Quinidine and Cinchonine are the most significant. These alkaloids occur in the bark as salts of organic acids. Cinchona bark is officially required to contain no less than 6% of total alkaloids of which not less than half must consist of Quinine and Cinchonidine. A good reference is Woodward, Doering, J. Amer. Chem. Soc. 66, 849 (1944). The greater part of the world's production of Cinchona has traditional medical use and is employed for the manufacture of Quinine which is used in large quantities as a specific against malaria. Extract of Cinchona, made by boiling 6.25 parts of the powdered bark with water for 10 minutes, cooling, straining and diluting to 100 parts is sometimes used as astringent gargles.

Tincture of Quillaia is generally made by the percolation process with 45% alcohol of the powdered bark obtained from Quillaja Saponaria, a large tree indigenous to Chile and Peru, belonging to the family Rosaceae. It occurs in commerce in yellow or reddish flat pieces about 100 cm in length and 10 or 15 cm broad. In fine powder Quillaia is extremely irritating to the nasal membranes and induces violent sneezing. This drug is also known as Soap Bark, Panama Wood, China Bark and Murillo Bark.

The physiologically active constituents are two saponin glucosides: Quillajic acid and quillaja sapotoxin; these two substances together form the saponin of commerce. A good quillaia should yield about 10% of the mixture. Reference: Cofman-Nicoresti, Pharm. J. 111, 103 (1923).

Tincture of quillaia finds its traditional medical use as an emulsifying agent. Also, a diluted extract is of benefit in the use as a detergent for use as a wash for the scalp and in the treatment of certain skin diseases, etc.

Tincture of Eucalyptus is made by triturating Eucalyptus Kino or Red Gum with three and a half times its weight of a mixture of 3 parts of glycerin and 5 parts of water, then adding alcohol and allowing to macerate for 12 hours. The mixture is filtered through cotton wool and diluted with more alcohol to produce a 1 in 10 tincture, and straining after 12 hours.

Eucalyptus Kino is obtained from various species of Australian and South American trees. It is often termed Red Gum and occurs in commerce as dark red irregular pieces about 1 cm or less in diameter.

Eucalyptus belongs to the family myrtaceae (order myrtales). Among the species rendering Kino, an astringent dark-reddish resin, obtained in a semifluid state from incisions made in the tree trunk, the following may be mentioned: E. Regnans, E. Salicifolia, E. Globulus, E. Siderophloia, E. Macrocarpa and E. Longirostris.

The major active ingredient in Eucalyptus Kino is approximately 41% tannin bodies, a variable proportion of Kino Red, catechin or catechol and moisture. Kino Red is formed by oxidation, induced by the presence of an oxydase enzyme and may be arrested by boiling the fresh solutions. Tincture of Eucalyptus is characterized in its medicinal applications by the astringent properties. The content of catechin may be determined with fair accuracy by taking advantage of the fact that this compound is soluble in hot but nearly insoluble in cold water. It may be obtained in small amounts by weighing about 0.5 grs. of the powdered residual Kino obtained by evaporation of the tincture of Eucalyptus and dissolve it in the least amount of hot water. When the solution is cold, the crystals of catechin are filtered in a Gooch crucible, washed with ice-cold water, dried at about 90 C. and weighed.

The invention may consist of the above naturally occurring ingredients in the following quantities:

|  |  | Volume Percent |
|---|---|---|
| Tincture of Cinchona | 40 c.c. | 8.6 |
| Tincture of Quillaia | 10 c.c. | 2.1 |
| Tincture of Eucalyptus | 10 c.c. | 2.1 |
| Ethyl Alcohol | 400 c.c. | 85.1 |
| Distilled Water | 10 c.c. | 2.1 |

The ingredients listed may be used in quantities different from those stated above depending upon the specific objectives desired from the composition. The quantities may be varied by as much as 25% without significant loss of efficacy.

In use, the scalp lotion has been found to be highly effective for treatment of seborrhea, for cleansing of the hair and the scalp and for improvement in the overall appearance of the hair, when applied externally by a qualified cosmetologist.

The scalp lotion, according to the invention, uses ingredients that are all organically derived from natural plant substances as described above. It avoids entirely the use of harsh chemicals that may be detrimental to the user and environmentally undesirable.

We claim:

1. A composition of organic ingredients, constituting an organic scalp lotion comprising in percent by volume:

8.6% Tincture of Cinchona containing Quinine and Cinchonidine and prepared from powdered bark of Cinchona plants;

2.1% Tincture of Quillaia containing Quillajic acid and quillaja sapotoxin and prepared from powdered bark of Qullaja Saponaria;

2.1% Tincture of Eucalyptus containing tannin, Kino Red and catechin and prepared from Red Gum of Eucalyptus plants;

85.1% ethyl alcohol; and 2.1% distilled water.

* * * * *